United States Patent [19]

Shiba et al.

[11] Patent Number: 4,669,875
[45] Date of Patent: Jun. 2, 1987

[54] FOREIGN PARTICLE DETECTING METHOD AND APPARATUS

[75] Inventors: Masataka Shiba; Sachio Uto; Mitsuyoshi Koizumi, all of Yokohama, Japan

[73] Assignee: Hitachi, Ltd., Tokyo, Japan

[21] Appl. No.: 548,516

[22] Filed: Nov. 3, 1983

[30] Foreign Application Priority Data

Nov. 4, 1982 [JP] Japan .................... 57-192462
Nov. 4, 1982 [JP] Japan .................... 57-192461
Feb. 21, 1983 [JP] Japan .................... 58-26156

[51] Int. Cl.$^4$ .......................... G01N 21/32
[52] U.S. Cl. ......................... 356/237; 250/572
[58] Field of Search ............... 356/237, 339, 343, 338; 250/572, 578

[56] References Cited

U.S. PATENT DOCUMENTS

| 2,947,212 | 8/1960 | Woods | 250/572 |
| 3,667,846 | 6/1972 | Nater et al. | 250/572 |
| 3,748,047 | 7/1973 | Millgood et al. | 250/572 |
| 4,342,515 | 8/1982 | Akiba et al. | 356/237 |
| 4,468,120 | 8/1984 | Tanimoto et al. | 356/237 |

FOREIGN PATENT DOCUMENTS 0133395 10/1979 Japan .................... 356/237

Primary Examiner—John E. Kittle
Assistant Examiner—José G. Dees
Attorney, Agent, or Firm—Antonelli, Terry & Wands

[57] ABSTRACT

The foreign particle detecting method and apparatus are disclosed wherein a polarized laser beam emitted by a laser beam irradiating system from a direction inclined with respect to the direction perpendicular to the surface of a substrate is used by a scanning means to linearly scan the substrate surface from a direction approximately 90° with respect to the laser light irradiating direction; and the laser light reflected from a foreign particle on the substrate surface is detected by a polarized light analyzer and a photoelectric conversion device from a direction set approximately equal to said scanning direction and inclined with respect to the direction perpendicular to the substrate surface.

20 Claims, 29 Drawing Figures

FIG. 10
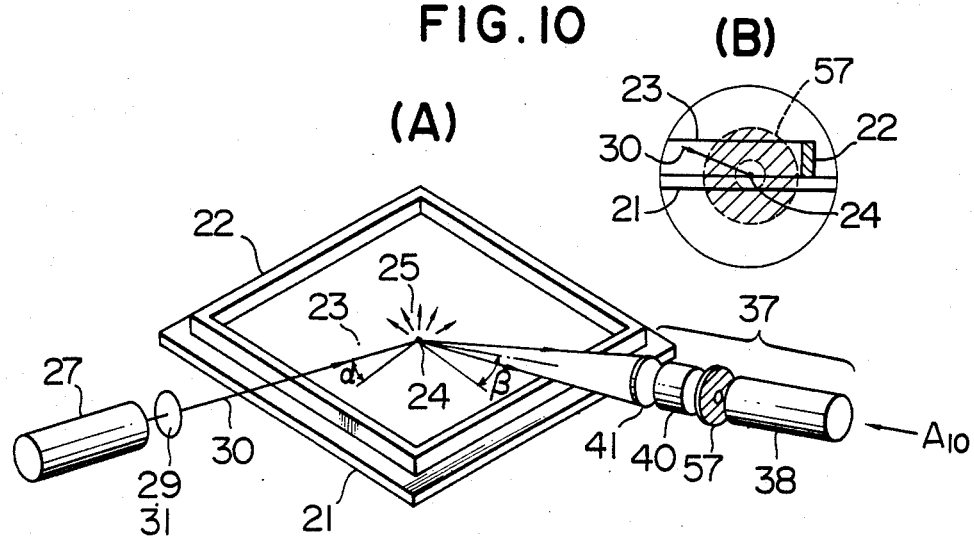
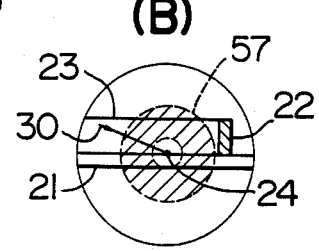
FIG. 11
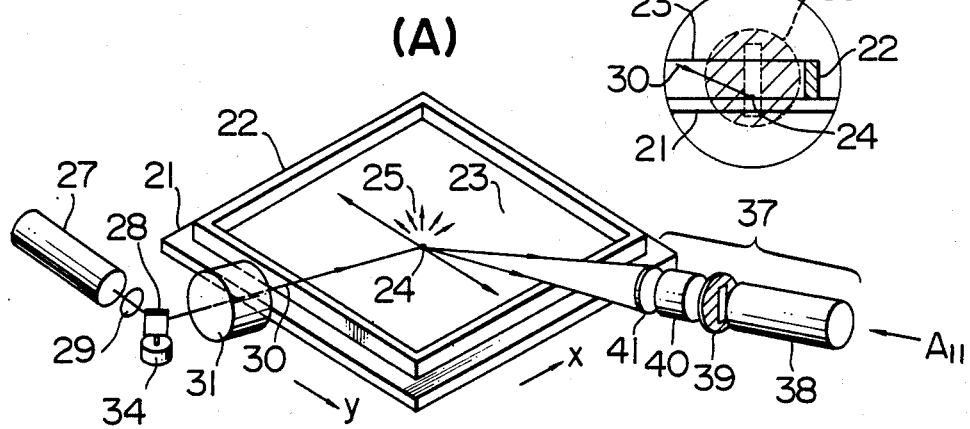
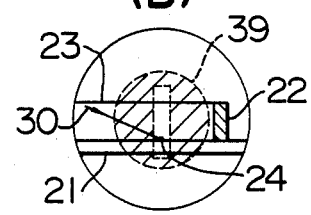

FIG. 12
(A) 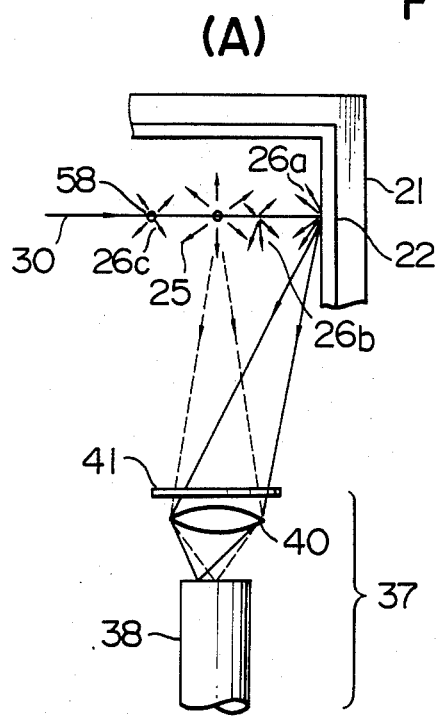
(B) 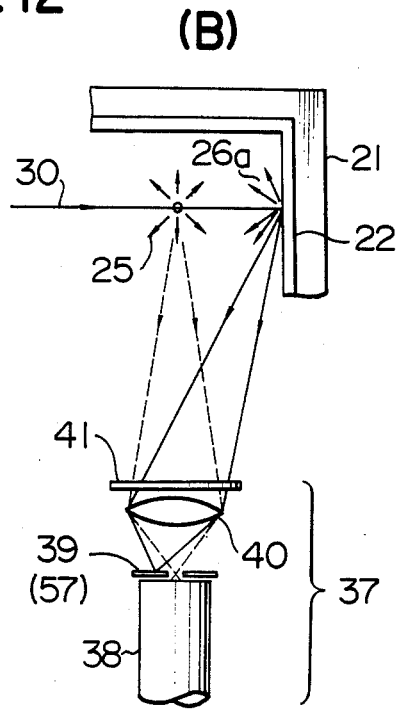
FIG. 13
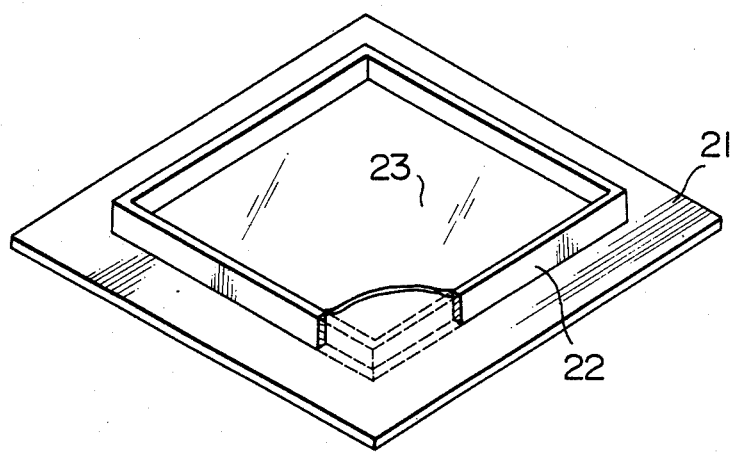

FIG. 21
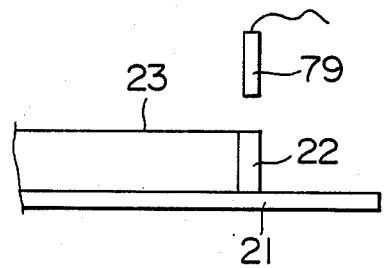
FIG. 22
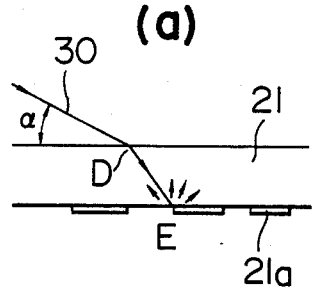
(a)
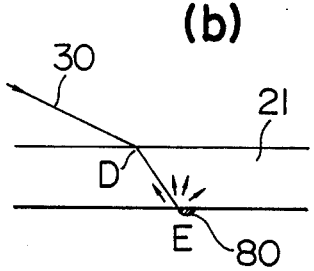
(b)
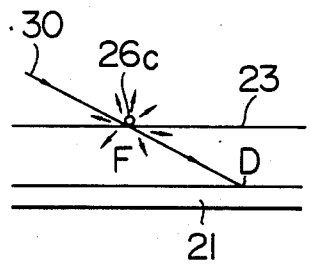
(c)
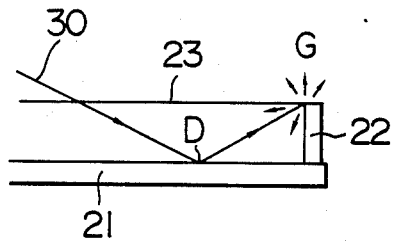
(d)

FIG. 29
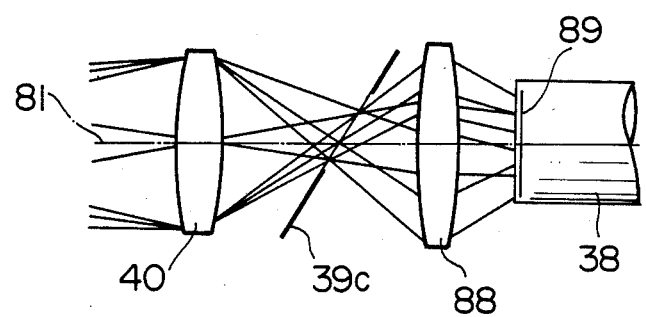
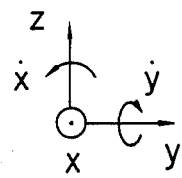

FOREIGN PARTICLE DETECTING METHOD AND APPARATUS

BACKGROUND OF THE INVENTION

1. Field of the Invention

The present invention relates to a method and apparatus for detecting foreign particles existing on the surface of a substrate.

2. Description of the Prior Art

The conventional foreign particle detecting apparatus is constructed, as disclosed in the U.S. Pat. No. 4,342,515, in a manner shown in FIG. 1. In this Figure, s-polarized laser beams 5, 6 from linearly polarized laser oscillators 3, 4 are irradiated to a foreign particle 2 on a wafer 1 sidewards along two directions, and a random polarized laser light 7 is scattered from the foreign particle 2. After the random polarized light 7 is focused by a condenser lens 8, only the s-polarized light of the condensed laser light is blocked by an analyzer 9; then, only a p-polarized light 10 is passed through a slit 11 for limiting the detection field and is detected by a photoelectric conversion device 12. On the other hand, the s-polarized light is scattered from an edge of a circuit pattern. Therefore, the presence of a foreign particle is recognized according to the output of the photoelectric conversion device 12.

In the conventional foreign particle detecting apparatus however, a wafer 1 being rotated must be fed along an axial direction of said wafer surface; hence, the foreign particle detecting speed is disadvantageously reduced.

SUMMARY OF THE INVENTION

An object of the present invention is to provide a method and apparatus for correctly detecting foreign particles existing on the substrate surface at a high speed by use of a simple construction whereby the above-mentioned disadvantage of the conventional apparatus is removed.

To achieve the object of the present invention, linearly polarized laser beam irradiated from a laser light irradiating means to a substrate from a direction inclined by 7.5° to 37.5° with respect to the surface of the substrate is linearly scanned on the substrate surface along the direction substantially 90° (90°±10°) relative to said irradiating direction by a scanning means comprising a rotating or swinging galvanomirror, polygonal mirror, prism, or the like. The scattered light from a foreign particle on the substrate is detected by a light analyzing means and a photoelectric converter in a direction substantially equal to the scanning direction and inclined by approximately 7.5° to 37.5° relative to the substrate surface.

On the other hand, if foreign particles exist on a reticle or photomask for a semiconductor exposure system, such as an automatic reduction projection mask aligner, when a pattern on the reticle or photomask is exposed onto a semiconductor wafer by a step-and-repeat way or the like, the latent images of the foreign particles are also exposed onto the wafer together with the circuit pattern and consequently all of the exposed portion (chip) on the completed wafer are rejected in some cases. As a counter-measurement to prevent adhesion of foreign particles, it has been considered to mount a so-called pellicle which comprises a pellicle thin film of nitrocellulose, etc. fixed to a frame formed of a metal or the like on a substrate, such as a reticle and photomask after the substrate is washed. The present invention enables to rapidly detect foreign particles on the substrate surface with high reliability without being affected by the frame of the pellicle even after the pellicle is mounted on the substrate; furthermore, the present invention enables to simplify the optical system for detecting the scattered light. Therefore, the foreign particle detecting apparatus according to the present invention comprises a light irradiating means for irradiating a light spot linearly scanning on the substrate from the direction inclined with respect to the direction perpendicular to the substrate surface so that an inclined linearly polarized light spot, such as a linearly polarized laser beam is irradiated alternately from two directions, and a scattered light detecting means for detecting a scattered light scattered on a foreign particle on the substrate surface in a direction substantially equal to an extended direction of said scanning line and inclined with respect to the direction perpendicular to the substrate surface, said scattered light detecting means being disposed at two symmetrical positions, said scattered light detecting means including a polarized light analyzer and a condenser lens for analyzing and condensing the scattered light of the foreign particles and a light receiving device for detecting the analyzed and condensed light. The present invention is characterized also by a pinhole- or a slit-shaped light blocking means disposed in the scattered light detecting system for preventing a malfunction to recognize the presence of a foreign matter on the substrate surface by receiving scattered light from the frame of the pellicle, the edge (step) of a circuit pattern of substrate, a foreign particle on the pellicle, or the like. Specifically, the present invention is characterized in that said foreign particle detecting apparatus includes said pinhole or slit provided at a position inclined relative to an optical axis of condenser lens so that in image formation by the condenser lens the scattered light obtained from other that the substrate surface is blocked.

Further, the present invention has the following characteristic: The positional relationship between the frame of the pellicle and the pellicled substrate is measured before inspection, thereby allowing to automatically set the effective inspection area.

Since the frame of pellicle is formed of a metal such as aluminum, the position of the frame can be measured by use of light reflection, light scattering, a mechanical contact sensor, or an electrostatic or magnetic noncontact sensor. This characteristic is advantageously utilized in the present invention.

BRIEF DESCRIPTION OF THE DRAWING

FIG. 10(A) is a diagram of the fundamental construction according to the present invention, wherein a pinhole-shaped light blocking means is added to the construction depicted in FIG. 3.

FIG. 10(B) is a magnified diagram of the portion of the diagram shown in FIG. 10(A) viewed from the direction A10.

FIG. 11(A) is a schematic diagram of a foreign particle detecting apparatus in which a slit-shaped light blocking means is disposed.

FIG. 11(B) is a magnified diagram of a portion of FIG. 10(A) viewed from the direction A11.

FIGS. 12(A) and 12(B) are diagrams depicting characteristics of the present invention.

FIG. 13 is a perspective side view of a pellicled substrate according to the present invention.

FIG. 21 is a side view of another embodiment of the pellicle frame position detecting means according to the present invention.

FIG. 22 is a diagram illustrating locations of abnormal scattered light viewed from the direction A shown in FIG. 23.

FIG. 29 is a diagram of the optical system employed as the scattered light detecting system of the present invention viewed from the direction C shown in FIG. 23.

DESCRIPTION OF THE PREFERRED EMBODIMENTS

Figure 1:
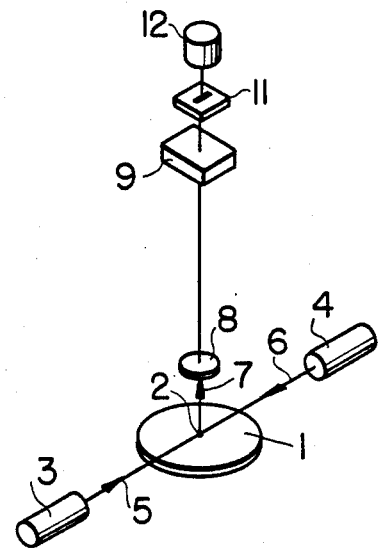
FIG. 1 is a schematic diagram of a conventional foreign particle detecting apparatus.
Figure 2:
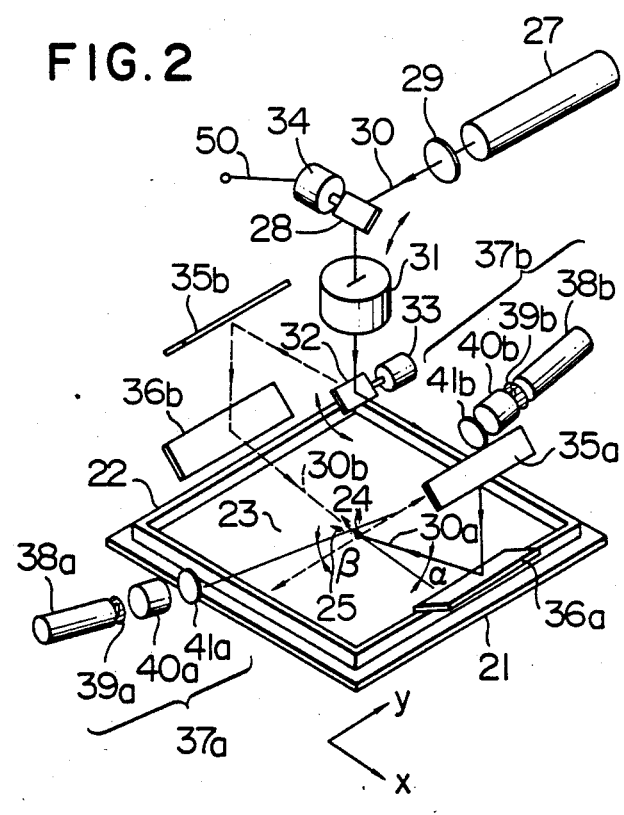
FIG. 2 is the exploded view of an embodiment of the present invention.

The present invention will be concretely described according to the embodiments in conjunction with the accompanying drawing. FIG. 2 shows an embodiment of an apparatus for detecting foreign particles on a substrate wherein a pellicle is mounted on a substrate of a photomask, reticle, or the like according to the present invention. A laser beam 30 emitted from a laser oscillator 27 is polarized by a polarizer 29 to be a linearly polarized wave having a predetermined polarization angle on a substrate (for example, to be an s-polarized laser) and is totally reflected on a galvanomirror 28 linked with a motor 34 which swings, then it is delivered to a mirror 32 through a f·$\theta$ lens 31. The laser beam further passes through mirrors 35a and 36a or mirrors 35b and 36b and is irradiated having a s-polarized light element (polarization vector is parallel to the substrate) on the surface of a substrate 21 from an inclined direction having an angle $\alpha$ with respect to the surface of a substrate 21. The galvanomirror 28 swings with a sawwave-shaped rotation, while the lens 31 is an f·$\theta$ lens which can scan the surface of the substrate 21 at a constant speed by use of a laser spot.

Figure 3:
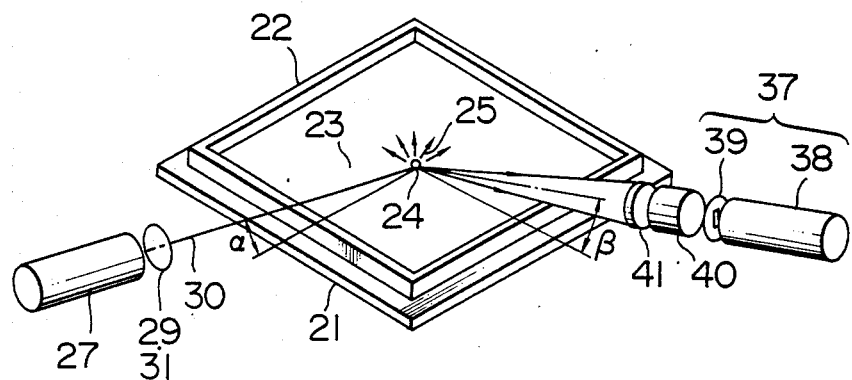
FIG. 3 is a diagram showing the fundamental construction according to the present invention.

A scattered light 25 from a foreign particle 24 existing on the surface of the substrate 21 shown in FIG. 3 becomes a random polarized light. Along a direction approximately parallel (0°±10°) to the laser scanning direction and inclined by 7.5° to 37.5° with respect to the surface of the substrate 21, the scattered light from a pattern (formed substantially in the 45° direction from the scanning direction) edge becomes a p-polarized light depending on the shape of a pattern edge or the like.

To detect the scattered light 25 (only s-polarized light) from the foreign particle 24 existing on the surface of the substrate 21 as shown in FIG. 2 two light detecting systems 37a and 37b are disposed at two positions symmetrical with respect to the y direction of the reticle substrate 21, each position being in a direction perpendicular to the respective laser light 30a or 30b (FIG. 2) and inclined upward by an angle $\beta$ with respect to the horizontal surface of the substrate 21. The scattered light detecting systems 37a and 37b comprise s-polarized light analyzers 41a and 41b by which p-polarized light from the pattern edge is blocked, condenser lenses 40a and 40b, slit-shaped light blocking means 39a and 39b, and photoelectric conversion devices 38a and 38b, respectively. The s-polarized light analyzers (41a) and (41b) extract linearly polarized waves having a predetermined polarization vector out of the scattered light 25 (FIG. 23) from the foreign particle 24. The light extracted through the s-polarized light analyzer is condensed by the condenser lenses 40a or 40b (FIG. 2) and reaches the photoelectric conversion device 38a or 38b through the slit-shaped light blocking means 39a or 39b. The photoelectric conversion device 38, such as a photoelectric multiplier having high sensitivity produces an electric signal proportional to the magnitude of a received light.

A pair of light irradiating means 35a, 36a and 35b, 36b; and a pair of light detecting systems 37a and 37b are provided in the means shown in FIG. 2 because of the following reasons.

Figure 5:
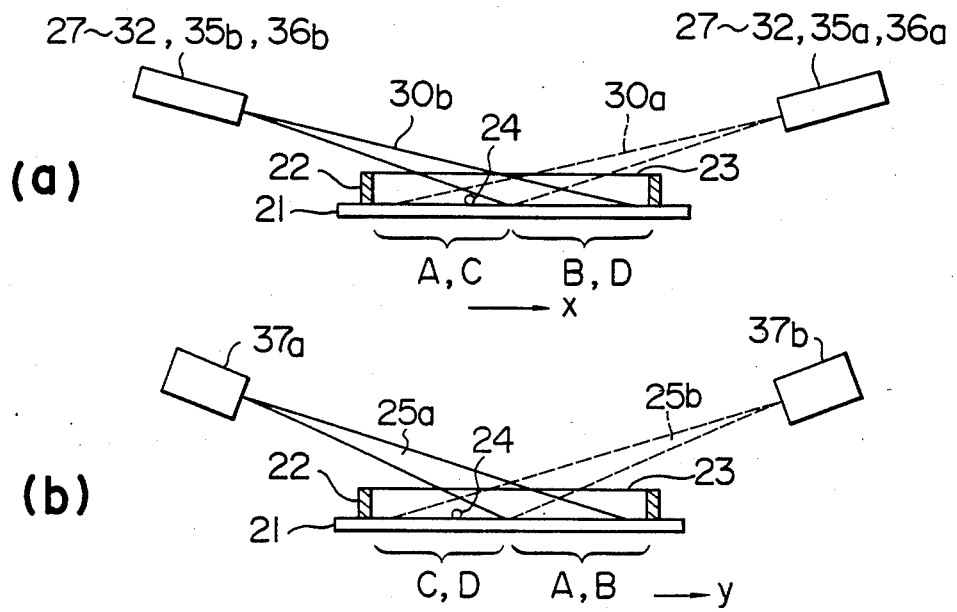
FIGS. 5a and 5b are cross-sectional diagrams showing the relationship between irradiated light and inspection area and that between the foreign particle detecting direction and the inspection area.
Figure 6:
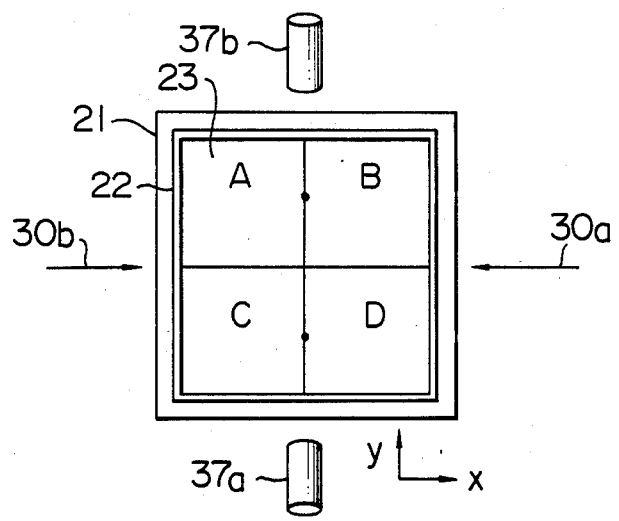
FIG. 6 is a schematic diagram illustrating the inspection area on a substrate.

FIGS. 5 and 6 illustrate irradiating directions of the laser beams 30a, 30b and detecting directions of a scattered light 25. To prevent the laser beams 30a and 30b and the scattered light 25 from the foreign particle 24 from being blocked by a pellicle frame (22), the substrate is subdivided into two parts as shown in FIG. 5 so that the laser beams 30a and 30b are always being irradiated from the opposite sides and the scattered light from the foreign particle 24 is detected from the opposite sides of the area in which the foreign particle 24 exists. That is, assuming that the inspection area on the substrate 21 is subdivided into four parts as illustrated in FIG. 6, the laser beam 30a is irradiated to inspection areas A and C, whereas the laser beam 30b is irradiated to inspection areas B and D. In this case, the laser beams 30a and 30b are alternately projected by turning the mirror 32 (FIG. 2) by 90° by a motor 33. The scattered light detecting systems 37a is actuated when the laser spot resides in the area A or B on the surface of the substrate 21, while the light detecting means 37b is actuated when the laser spot resides in the area C or D on the surface of the substrate 21. This means that the scattered light detection signal of the photoelectric conversion device 38a or 38b such as a photoelectric multiplier is turned on or off in synchronism with the rotation angle of the galvanomirror 28. Since the detecting sensibility for the scattered light 25 from a foreign particle 24 varies between the case where the foreign particle resides in the vicinity of the center of the substrate 21 (FIG. 2) and the case where it resides in a peripheral location thereof, the electrical threshold value (slice level) for detecting a foreign particle can be changed, in synchronism with the position of the laser spot residing on the surface of the substrate 21 in the present foreign particle detecting apparatus.

Figure 7:
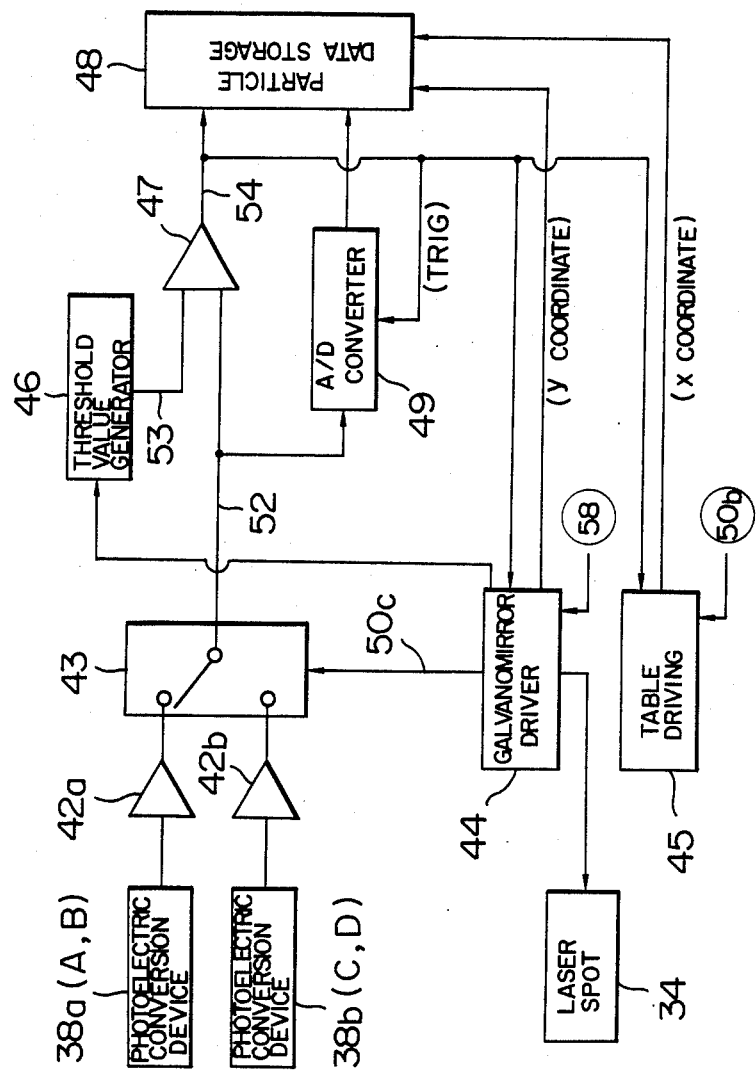
FIG. 7 shows the electric circuit according to the present invention.
Figure 8:
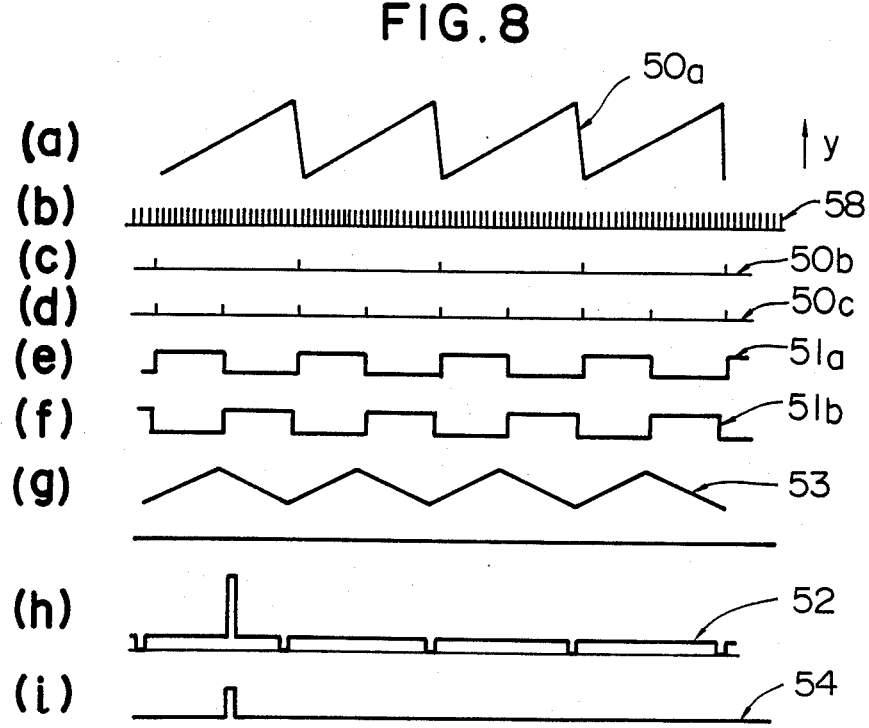
FIG. 8 is a signal waveform diagram obtaine by the circuit shown in FIG. 7.
Figure 9:
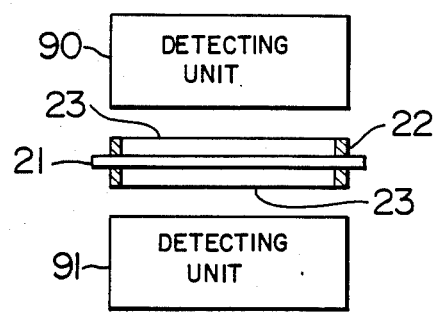
FIG. 9 is a schematic diagram illustrating the construction of an apparatus for inspecting the upper and lower surfaces of a substrate.

FIG. 7 outlines the scattered light detecting circuit configuration. Analog signals output from the photoelectric conversion devices 38a and 38b are inputted to a multiplexer 43 through voltage amplifiers 42a and 42b, respectively. The multiplexer 43 is switched by a change-over pulse 50c (shown as (d) in FIG. 8) in synchronism with a timing pulse 50b (depicted as (c) in FIG. 8) to be generated by a driving signal 50a (illustrated as (a) in FIG. 8) output from a galvanomirror driving circuit 44 in proportion to the rotation angle. For the areas A and B, the photoelectric conversion device 37a (signal 38a) is selected as indicated by a signal 51a (shown as (e) in FIG. 8); whereas for the areas C and D, the photoelectric conversion device 37b (signal 38b) is selected as indicated by a signal 51b (depicted as (f) in FIG. 8). In a comparator 47 (for handling the threshold value), an analog signal 52 shown as (h) in FIG. 8 is compared with a variable threshold value signal 53 (shown as (g) in FIG. 8) generated by a threshold value generator circuit 46 for varying voltage synchronized with an electric signal output from the galvanomirror driving circuit 44. As a result, a signal 54 shown as (i) in FIG. 8 is obtained. If the value of the detection signal 52 exceeds the threshold value 53 in this case, the peak value of the detection signal 52 is stored in a particle data storage 48 by use of an A/D converter 49; and at the same time, a clock pulse signal (shown as (b) in FIG. 8) which generates a driving signal of the galvanomirror driving circuit 44 is converted into the y coordinate of a point on the substrate 21 and an electric signal of an x coordinate detecting sensor obtained from a table driving circuit 45 or a signal obtained by accumulating signals 50b (shown as (c) in FIG. 8) is converted into the x coordinate of the point on the substrate 21. Consequently, the coordinate (x, y) of the position at which the foreign particle exists is obtained, thus the dimensions and the shape of the foreign particle can be observed by a means, such as a microscope, after the foreign particle is detected.

The explanation above applies to a detecting unit 90 for detecting foreign particles on the upper surface of the substrate 21. To detect foreign particles on the lower surface of the substrate 21, a detecting unit 91 for detecting foreign particles on the lower surfaces need only be disposed below the substrate 21. In this case, the construction and electric circuit configuration are completely the same.

Since foreign particles having their sizes from 5 $\mu$m to 10 $\mu$m must be detected on the upper surface of a reticle and those having sizes from 2 $\mu$m to 5 $\mu$m must be detected on the lower pattern surface for a reticle of a reduction projection type mask aligner, the threshold values of the detecting units 90 and 91 for the upper and lower surfaces must be set to the levels for detecting said foreign particles, respectively.

Figure 4:
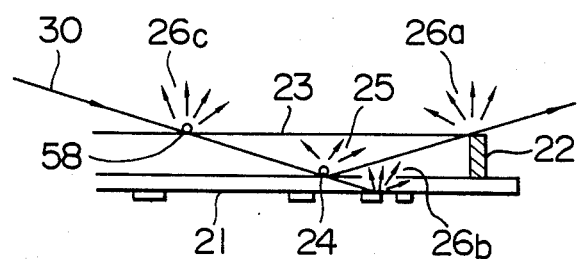
FIG. 4 is a schematic cross-sectional diagram illustrating the influence of a pellicle frame.

According to the present invention as explained above, to prevent influence of a pellicle frame 22 (for example, thickness: 2 mm, height: 4 mm or 6.3 mm) or a 107 mm pellicle mounted on the surface of a substrate, the irradiating optics 27 and 29, 31 are disposed at positions ($\alpha$(FIGS. 2 and 3)=22.5°±15°) which allow the irradiating means 27 and 29, 31 to irradiate light on the substrate surface without being affected by the pellicle frame, and a scattered light detecting systems 37 is disposed along a line which is drawn substantially perpendicular (90°±10°) to the line along which the irradiating means 27 and 29 are placed and which is inclined upward ($\beta$(FIGS. 2 and 3)=22.5°±15°) with respect to the substrate surface, thereby enabling to detect foreign particles on the surface of the substrate 21. However, as shown in FIG. 4 since the laser beam is irradiated on the substrate 21 along an inclined direction, a scattered light 26a from the upper surface of the pellicle frame 22, a scattered light 26b from a reticle pattern surface, or a scattered light 26c from a foreign particle 58 on a pellicle 23 is erroneously detected as a foreign particle 24 on the surface of the substrate 21.

In the present invention, the erroneous detection is prevented by adding a pinhole-shaped light blocking means 57 illustrated in FIG. 10 and the slit-shaped light blocking means 39 depicted in FIG. 11 to the foreign particle detecting apparatus. To detect foreign particles on the substrate surface by use of the foreign particle detecting apparatus to which the pinhole-shaped light blocking means 57 shown in FIG. 10 is added, the substrate 21 must be scanned in two directions (2-dimensional scanning) by mounting the substrate on a table (not shown) which travels along a direction while moving to the x-axis or y-axis direction or rotating. To detect foreign particles on the substrate surface by using the foreign particle detecting apparatus to which the slit-shaped light blocking means 39 is added, the laser beam scanning is performed along a direction (y-axis direction) by a scanning means (comprising the galvanomirror 28, f-$\theta$ lens 31, etc.) while the substrate mounted on an x-direction table (not shown) is being moved to the direction (x-axis direction) perpendicular to the laser beam scanning direction. Adoption of the pinhole-shaped or slit-shaped light blocking means shown in FIGS. 10 and 11, respectively as explained above allows to detect foreign particles on the substrate surface with high sensibility without being affected by the scattered light, for example, from the pellicle frame shown in FIG. 12.

FIG. 13 illustrates a pellicle mounted on the substrate for preventing foreign particles from adhering to the substrate 21. The pellicle comprises the pellicle thin film 23 and the frame 22. The frame 22 is adhered to the substrate 21 by use of adhesive, double-sided adhesive tape, or the like.

Figure 14:
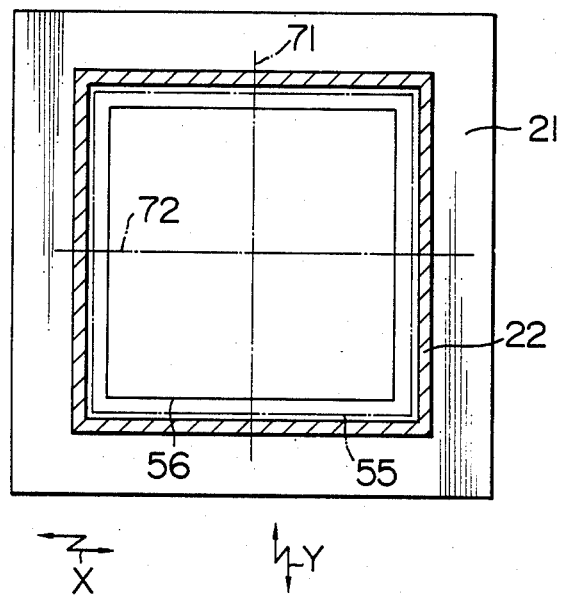
FIG. 14 is a front view of a substrate.

To detect foreign particles on the substrate 21 enclosed with the pellicle frame 22, an effective inspection area 55 in the area enclosed with the frame 22 must be specified as shown in FIG. 14. Reference numeral 56 indicates the pattern area on the substrate 21. Since the relative mounting position of the frame 22 on the substrate 21 is not exact in general, the interference between the effective inspection area 55 and the frame 22 must be prevented.

For this purpose, an s-polarized laser beam 30, which is oscillated from the laser oscillator 27 and polarized by the s-polarizer, through the f-θ lens 31 as shown in FIG. 3 is irradiated on the substrate 21 to form the laser spot from a direction inclined by an angle of incidence $\alpha = 22.5° \pm 15°$). Scattered lights from the pattern and foreign particles are detected by a detecting system 37 disposed approximately perpendicularly (90°±10°) to the line along which the s-polarized laser light 10 is irradiated. In this case, the light scattered only from the foreign particles can be extracted by using the analyzer 41 which passes only the s-polarized light. The condenser lens 40 and slit 39 block the scattered light from other than the scanning line of the spot 24. The scattered light detecting system 37 is disposed along an inclined line with an angle $\beta$ equal to $22.5° \pm 15°$ to prevent the interference from the pellicle frame 22. The interference from the frame 22 can be prevented also when the pellicle 23 is mounted on the substrate 21 by disposing the scattered light detecting systems 37a and 37b as shown in FIG. 2 and by alternating the laser beams 30a and 30b and the scattered light detecting systems 37a and 37b, respectively.

Next, an embodiment of the present invention will be explained in which the position of the pellicle frame is obtained by the scattered light detecting function of the foreign particle detecting apparatus.

Figure 15:
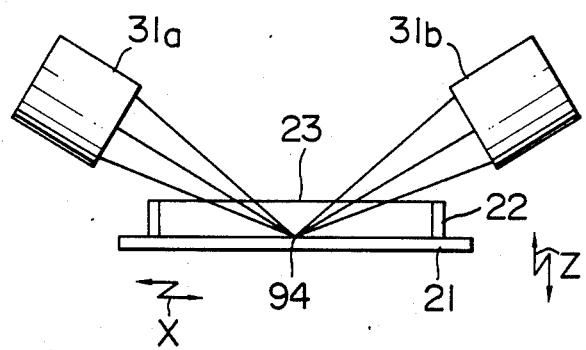
FIGS. 15 and 16 are side views of a substrate, respectively.
Figure 16:
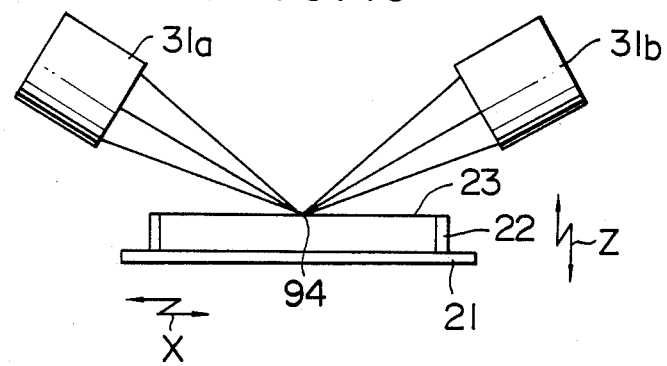
Figure 17:
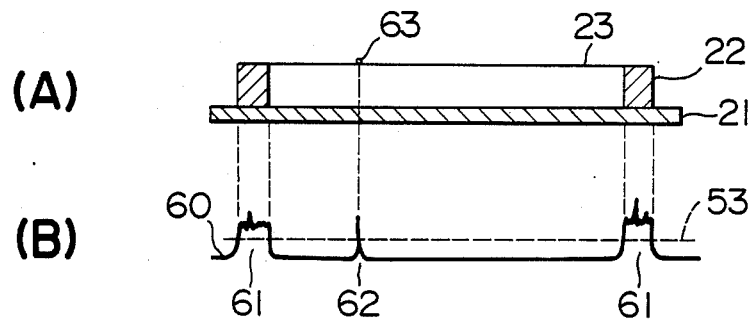
FIG. 17 is a representation of output signals corresponding to respective portions of a substrate.

FIG. 15 illustrates the optical system viewed from the Y direction. The laser spot 94 is formed on the substrate 21 through the f-θ lens 31a or 31b. The spot 94 is formed on the pellicle surface 23 by moving the substrate 21 in the Z direction as depicted in FIG. 16. If the laser spot 94 scanning is performed in the X and Y directions under this condition, a photoelectric multiplier output 60 indicated as (B) corresponding to the diagram indicated as (A) in FIG. 17 is obtained according to light scattered on the frame 22 when the spot 94 comes to the frame 22. In the diagram depicted as (B) in FIG. 17, the reference numerals 53, 61, and 62 indicate a threshold value, the peak value caused by the frame 22, and the peak value caused by a foreign particle 63, respectively.

Figure 18:
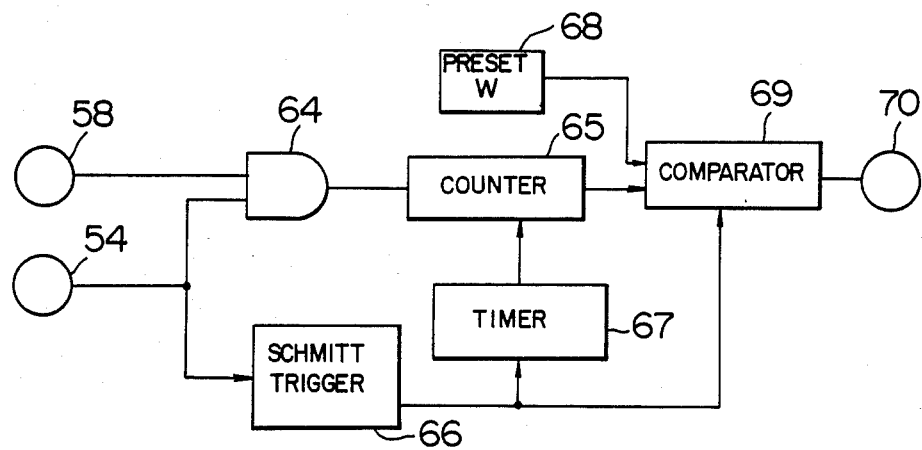
FIG. 18 is a diagram showing a circuit for discriminating a frame position.

FIG. 18 depicts an electric circuit for discriminating the peak value 61 caused by the frame 22 from the peak value 62 caused by the foreign particle 63. The time period in which the signal 54 indicating that the level of the photoelectric multiplier exceeds the threshold value 53 in FIG. 8 is on is measured by a counter 65 counting the clock signal 58. When the level becomes equal to or less than the threshold value 53 and the signal 54 turns off, the falling edge of the signal 54 is detected by a Schmitt-trigger circuit 66 to produce a reset signal, which resets a comparator 69 and the counter output counted so far is compared with a preset value w by the comparator 69 to generate a signal 70. Then, the counter 65 is reset by the reset signal through a timer 67. If the preset value (clock count) w is less than the value of the counter 65, the detected light is assumed to be scattered from the frame; otherwise, it is assumed to be scattered from a foreign particle. This operation is performed along reticle central lines 71 and 72 shown in FIG. 14 to determine the frame positions with respect to x and y axes, then the effective inspection area 55 is determined in the frame with a space disposed between each side of the effective inspection area 55 and the corresponding side of the frame 22.

Figure 19:
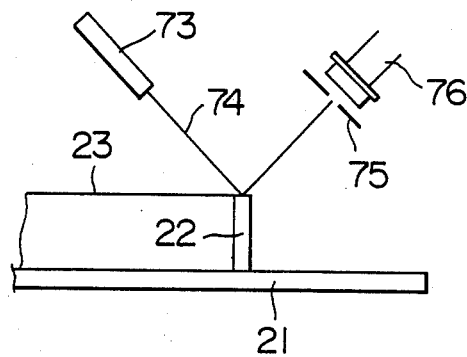
FIG. 19 is a side view of an embodiment of the pellicle frame position detecting means according to the present invention.

Next, an embodiment of the present invention will be explained in conjunction with FIG. 19, wherein the frame mounting position is measured by use of the magnitude of the reflected light. A laser beam 74 from a laser tube 73 or the like is irradiated on the pellicle 23 along a line drawn upward relative to the pellicle, and the reflected light is received by a light receiving device 76 through a slit 75. If the laser beam 74 is projected on the pellicle 23 which has not the frame 22 thereunder, the light is passed through the pellicle, hence the light reception level is low; if the frame is disposed under the pellicle, the regular reflection therefrom is received by the light receiving device 76, hence the light reception level increases and the frame mounting position is detected. A sensor operating as explained above is disposed in a portion of the foreign particle detecting apparatus.

Figure 20:
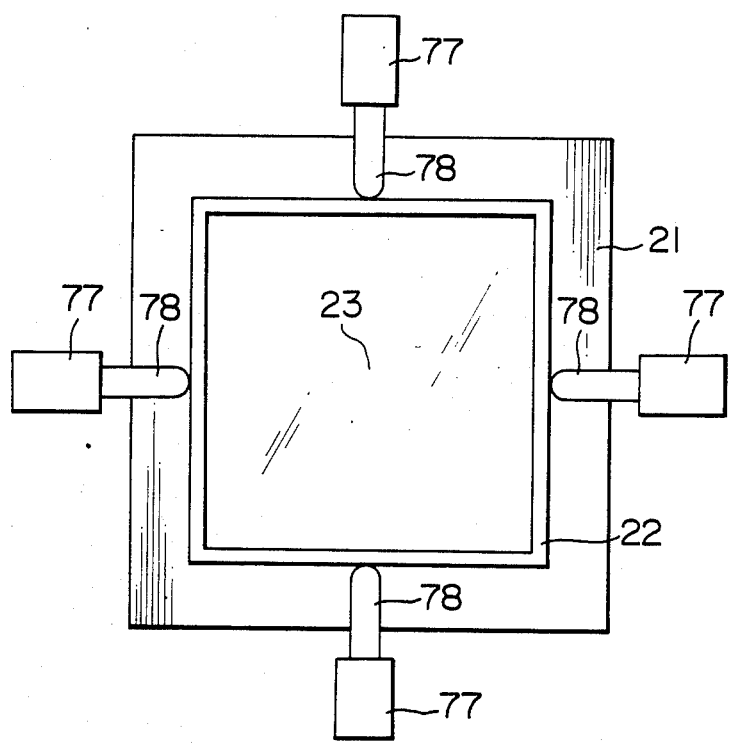
FIG. 20 is a front view of still another embodiment of a pellicle frame position detecting means according to the present invention.

FIG. 20 shows another embodiment of the present invention in which a mechanical contact sensor is utilized. A pin 78 is pressed against the frame 22 and the amount of pin movement is measured by a position detecting sensor 77, thereby calculating the frame position.

FIG. 21 depicts still another embodiment of the present invention in which the pellicle frame 22 is formed with a magnetic material and a noncontact electromagnetic sensor 79 is used to detect the frame position.

If the foreign particle detection must be performed on the upper and lower surfaces of a substrate, the frame position detecting means need not only be disposed on each surface.

According to the present embodiment, since the effective inspection area of foreign particles on the substrate on which the pellicle is mounted can be set automatically, operational procedures become simple even if there is fluctuation in the position for mounting the pellicle. Moreover, the frame can be discriminated from foreign particles, thus the foreign particle detecting performance is remarkably improved.

FIGS. 22(a) to 22(d) show a diagram of light scattering position viewed from the y direction, illustrating the locations of abnormally scattered light that can be detected by the foreign particle detecting system.

When the laser beam 30 is irradiated to the point D on the foreign particle detecting surface along a line inclined by $\alpha$ degree (7.5° to 37.5°), the refracted light reaches the lower surface E because the substrate 21 is transparent. If the pattern 21a ((a) in FIG. 22) or a foreign particle 80 ((b) in FIG. 22) exists at the position where the refracted light reaches, the scattered light therefrom can be detected. With a pellicle mounted on the substrate, if a large foreign particle 26c exists at the position F where the laser beam 30 passes through the pellicle 23 on the substrate 21 ((c) in FIG. 22) or if the light reflected on the surface of the substrate 21 hits the position G on the edge of the metal frame 22 of the pellicle ((d) in FIG. 22), the scattered light can be detected. Consequently, hindrances on the lower surface of the substrate, pellicle, or the like may cause erroneous foreign particle detection in procedures explained above.

To overcome this difficulty according to the present invention, the slit 39 is disposed between the condenser lens 40 and photoelectric multiplier 38 to block the scattered light from other than the detecting surface of the substrate, thereby enabling to detect only foreign particles existing on the substrate. Details will be explained as follows. FIG. 24 is the diagram of the location of abnormally scattered light shown in FIG. 23 viewed from the upper surface of the substrate. As illustrated in FIG. 24, the laser beam 30 may be scattered at points D, E, F, and G. When a portion of the scattered light is focused by the condenser lens 40, the corresponding spots D', E', F', and G' are imaged on the image focusing plane 82. If the slit 39 is disposed to block only the abnormally scattered light corresponding to the points E', F', and G', only the scattered light from the point D' to be inspected can be received by the photoelectric multiplier 38. The optical axis of the condenser lens 40 exists on the plane where the extended portion of the scanning line 80 of the laser beam 30 is found.

Figure 23:
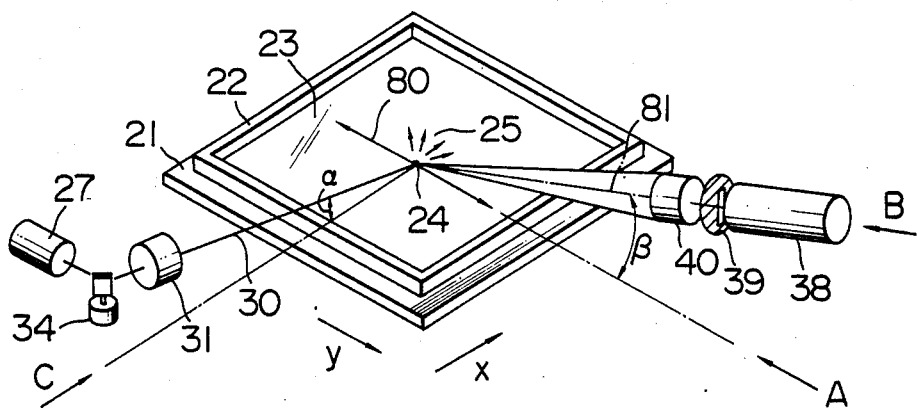
FIG. 23 is a view showing another embodiment of the foreign particle detecting apparatus according to the present invention.
Figure 24:
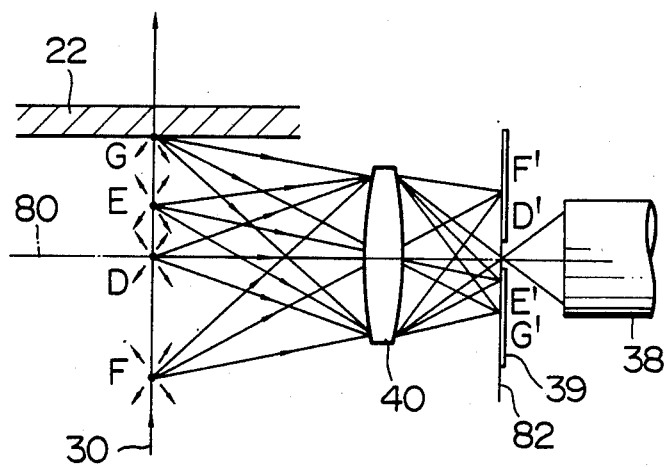
FIG. 24 is a schematic diagram illustrating the method for blocking abnormally scattered light according to the present invention.
Figure 25:
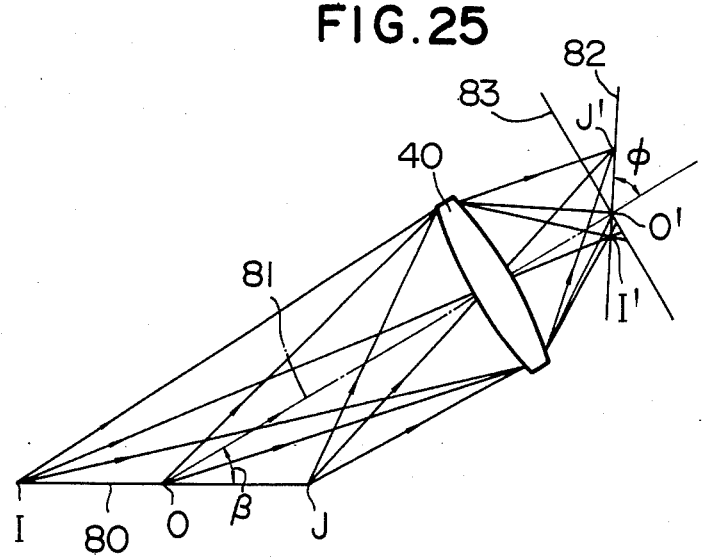
FIG. 25 is a view for explaining the principle of the slit action in conjunction with the light passing therethrough.

On the other hand, FIG. 25 shows a diagram corresponding to that depicted in FIG. 23 viewed from the direction C. The optical axis 81 of the condenser lens 40 is inclined by $\beta$ degrees with respect to the laser beam scanning line 80. The scattered light emitted from the positions I, O, and J on the scanning line 80 is imaged as the points I', O', and J' on the image focusing plane 82. Therefore, a slit-shaped light blocking plate 39 (FIG. 23) is adopted. The light blocking plate 39 allows to detect only foreign particles existing on the transparent substrate 21. That is, the scattered light only from the point D (FIG. 24) on the transparent substrate 21 can be detected.

Figure 26:
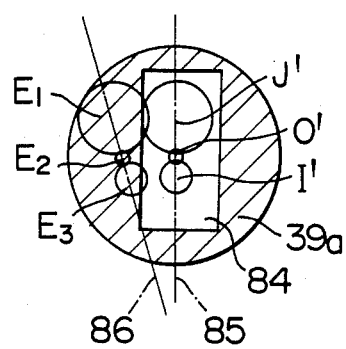
FIGS. 26, 27, and 28 are view showing the shapes of the slit viewed from the direction B shown in FIG. 23.

If the slit 39 is disposed on a plane 83 perpendicular to the optical axis 81 of the focusing lens, points other than those on the optical axis are defocused, hence the effect for blocking the abnormally scattered light is suppressed as shown in FIG. 26. Reference numerals 39a, 88, and 85 indicate the slit plate, the aperture of the slit plate, and the image focusing trace produced by the scanning line for detecting foreign particles, respectively; further, reference numeral 86 indicates a focusing trace of the scattered light from the lower surface and $E_1$ and $E_3$ represent the sizes of spots made by abnormally scattered light. As can be seen from this diagram, the overlapped portion with the scattered light to be detected, so that discrimination of the abnormally scattered light from the scattered light to be detected becomes impossible.

However, if the slit 39b is inclined to fall just on to the image focusing plane 82 depicted in FIG. 25, the slit condition becomes as shown in FIG. 26, thus the discrimination between the scattered lights explained above is enabled.

In this case, the inclination $\phi$ of the image focusing plane is given by the following formula, $$\tan\phi = \frac{1}{m} \tan\beta$$

where m is the magnification of the condenser lens 40 on the optical axis 81. When the value of m is great, the value of $\phi$ becomes small and the inclination of the slit increases, so the light detection becomes difficult. For example, if the value of m is set as approximately 0.27 for the $\beta$ equals to 15°, the value of $\phi$ is approximately 45°, hence it is possible to dispose the slit easily. Although the condition varies depending on the value of $\beta$, the magnification of the condenser lens must be equal to or less than one.

Figure 27:
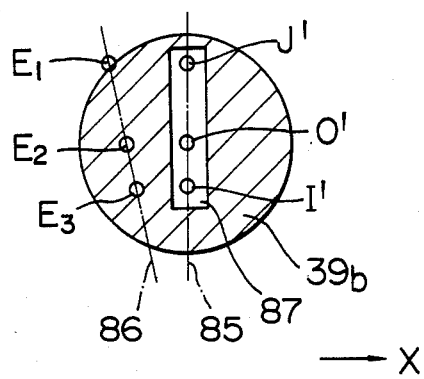

Since the spot size of the laser beam irradiated on the transparent substrate is fixed, the sizes of spot images of I', O', and J' obtained by focusing the spots I, O, and J as shown in FIG. 25 vary because of the different magnification. This applies also to the traces of abnormally scattered light, thus the lines 86 and 85 are not parallel in FIGS. 26 and 27.

Figure 28:
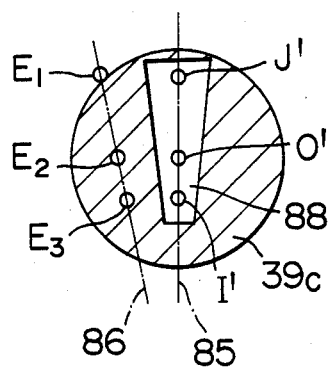

To retain a satisfactory discriminating ratio between foreign particle and the others and to increase the tolerance for the fluctuation of a spot in the X direction based on above-mentioned characteristics, the shape of the slit 39c need only be modified as illustrated in FIG. 28. In this case, the width of the slit 39C must be greater than the size of a laser spot image including the effect of the aberration caused by the condenser lens.

Although the slit is placed between the condenser lens 40 and the photoelectric multiplier 38, it is further preferable to disperse a field lens 88 for focusing light between the slit 39c and the photoelectric multiplier 38. This is because the photoelectric multiplier cannot be placed sufficiently near the slit due to the inclination of the slit, and the scattered light cannot be gathered on a light receiving surface 89 of the photoelectric multiplier without the field lens.

A scattered light detecting optical system is constructed based on the configuration depicted in FIG. 29. The scattered light detecting sensitivity is improved by inserting an ND filter at an intermediate point of the optical path in some cases.

When the slit 39c is installed, the slit position must be correctly arranged relative to the laser beam scanning line trace produced by the condenser lens. For this purpose, a fine adjustment mechanism must be provided only for the slit in the scattered light detecting optical system. In FIG. 29, at least fine adjustment in the x and y directions is indispensable, hence a rotating fine adjusting mechanism for the x- and y-directional adjustment is provided if necessary.

According to the present embodiment, since the abnormally scattered light from the pattern and foreign particles on the lower surface of the substrate, the pellicle and the like which may hinder the proper inspection can be completely ignored, the rate of erroneous foreign particle detection is reduced, the time period required for the visual check after the automatic inspection is minimized, and the number of cleaning operations is decreased; thereby contributing to the production cost reduction and productivity improvement.

According to the present invention as explained above, the foreign particle inspection can be conducted with a simple foreign particle detecting apparatus which detects foreign particles on a substrate at a high speed while feeding the substrate to a predetermined direction. Furthermore, the magnitude of the scattered light from foreign particles can be effectively detected without being affected by the pellicle frame on the substrate surface and the circuit pattern formed on the substrate, wherein a particle as small as 2 $\mu$m can be detected. As the inclination angles $\alpha$ and $\beta$ decreases, the change in the polarization angle can be more effectively detected. Although the detecting sensitivity is improved in this case, the inclination angles $\alpha$ and $\beta$ are preferably set as 22.5°±15° because of the influence from the pellicle frame.

What is claimed is:

1. A foreign particle detecting method comprising the steps of:
    irradiating two halves of a substrate having a frame with a pellicle mounted thereon with a respective laser beam emitted by a laser beam irradiating means in a direction inclined with respect to the substrate surface and polarized thereafter so as to scan respective halves of the substrate surface in a predetermined direction while linearly moving said substrate in a direction crossing at substantially right angles to the light scanning direction;

positioning, at least prior to the step of irradiating, a respective polarized-light analyzer in said scanning direction inclined with respect to said substrate surface for analyzing the scattered light from a foreign particle on respective halves of the substrate; and detecting said scattered light by a photo-electric conversion means;

whereby the entirety of the substrate is enabled to be inspected for detection of foreign particles irrespective of the frame and pellicle mounted on the substrate.

2. A foreign particle detecting method comprising the steps of:

irradiating two halves of a substrate, through a preventive means mounted on the substrate by a frame for preventing adherence of foreign particles to the substrate, with a respective laser beam emitted by a laser beam irradiating means in a direction inclined with respect to the substrate surface so as to scan respective halves the substrate surface which is covered with said preventive means in a predetermined direction while linearly moving said substrate in a direction substantially 90° with respect to the laser beam crossing at substantially right angles to the light scanning direction;

positioning, at least prior to the step of irradiating, a respective polarized-light analyzer in said scanning direction inclined with respect to said substrate surface for analyzing the scattered light from a foreign particle on respective halves of the substrate; and detecting said scattered light by a photoelectric conversion means; wherein the entirety of the substrate is enabled to be inspected for detection of foreign particles irrespective of the frame and preventive means mounted on the substrate.

3. A foreign particle detecting apparatus comprising: irradiating means for irradiating a respective polarized laser beam spot linearly scanning on respective halves of two halves of a substrate in a direction inclined with respect to the direction perpendicular to the surface of the substrate placed on a horizontal plane and having a frame with a pellicle mounted thereon, said irradiating means including a laser beam oscillator and a polarizer; scattered light detecting means for detecting scattered light from a foreign particle in the laser beam spot on respective halves of the surface of the substrate, said scattered light detecting means being positioned along an extended direction of said scanning line and being inclined with respect to the direction perpendicular to the surface of the substrate, said scattered light detecting means including a polarized light analyzer, condenser lens, and photoelectric converter, whereby the entirety of the substrate is enabled to be inspected for detection of foreign particles irrespective of the frame and pellicle mounted on the substrate.

4. A foreign particle detecting apparatus according to claim 3, comprising a light blocking means disposed between said condenser lens and photoelectric converter of said scattered light detecting means.

5. A foreign particle detecting apparatus according to claim 3 wherein the inclination angle of at least one of said optical axis of the irradiating means and scattered light detecting means is 22.5°±15°.

6. A foreign particle detecting apparatus according to claim 3 wherein said optical axes of the irradiating means and the scattered light detecting means intersect each other at angle of 90°±10° on said surface of the substrate.

7. A foreign particle detecting apparatus comprising:
frame position detecting means for detecting a position of a frame of a pellicle mounted on a substrate; and detection means for detecting a foreign particle existing in the inspection area enclosed with said frame according to the frame mounting position detected by said frame position detecting means.

8. A foreign particle detecting apparatus comprising:
laser beam irradiating means for irradiating two halves of a substrate having a frame with a pellicle mounted thereon with a respective polarized laser beam spot, each of said laser beam spots being scanned over one half of the substrate in a direction inclined with respect to a direction perpendicular to the surface of the substrate; and a pair of light detecting means positioned in the direction along which said scanning line is extended for detecting scattered light from a foreign particle on respective halves of the substrate, for analyzing the scattered light by a polarized light analyzer, for condensing the scattered light by a condenser lens, and for detecting the image formation obtained from said condenser lens by a photoelectric converting means, wherein blocking means for blocking the light scattered from other than the surface of said substrate is disposed between said condenser lens and said photoelectric converting means;

whereby the entirety of the substrate is enabled to be inspected for detection of foreign particles irrespective of the frame and pellicle mounted on the substrate.

9. A foreign particle detecting apparatus according to claim 8 wherein said blocking means of said scattered light detecting means is disposed along a direction inclined with respect to the optical axis of said condenser lens.

10. A foreign particle detecting apparatus according to claim 9 wherein the magnification of said condenser lens of said scattered light detecting means is equal to or less than one.

11. A foreign particle detecting apparatus according to claim 9 wherein said blocking means is formed by a slit.

12. A foreign particle detecting apparatus according to claim 11 wherein the width of said slit of said blocking means changes in the longitudinal direction.

13. A foreign particle detecting apparatus according to claim 8 wherein at least a pair of said irradiating means are disposed opposing to each other with respect to said substrate, at least a pair of said light detecting means is disposed opposing to each other with respect to said substrate.

14. A foreign particle detecting apparatus comprising:
projecting means including;
a laser source;

a rotating mirror for performing scanning by use of a laser beam projected from said laser source in a predetermined direction;

a changeover mirror for changing over the direction of the laser beam by reflecting said laser beam outputted from said rotating mirror;

a pair of projecting optical systems, each of said projecting optical systems being arranged for projecting said laser beam changed over by said changeover mirror as a laser spot from a direction inclined with respect to a substrate having a frame with a pellicle mounted thereon so that said laser beam projected by one of said projecting optical systems is projected in a direction opposite to the direction of projecting of said laser beam by the other of said projecting systems for scanning different halve of said substrate; and at least a pair of detecting means disposed opposing to each other with respect to said substrate, which detects from an inclined direction with respect to said substrate, scattered light from a foreign particle existing in the laser spot on the different halves of said substrate projected by said projecting optical systems through a polarized-light analyzer and a condenser lens and for providing output electric signals by photoelectric converting means disposed along each axis of said pair of detecting means;

whereby the entirety of the substrate is enabled to be inspected for detection of foreign particles irrespective of the frame and pellicle mounted on the substrate.

15. A foreign particle detecting apparatus comprising:

projecting means including;

a laser source;

a rotating mirror for performing scanning by use of a laser beam projected from said laser source in a predetermined direction;

a changeover mirror for changing over the direction of the laser beam by reflecting said laser beam outputted from said rotating mirror;

a pair of projecting optical systems, each of said projecting optical systems being arranged for projecting said laser beam changed over by said changeover mirror as a laser spot from a direction inclined with respect to a substrate so that said laser beam projected by one of said projecting optical systems is projected in a direction opposite to the direction of projection of said laser beam by the other of said projecting optical systems;

at least a pair of detecting means disposed opposing to each other with respect to said substrate, which detects from an inclined direction with respect to said substrate, scattered light from a foreign particle, existing in the laser spot on said substrate projected by said projecting optical systems through a polarized-light analyzer and a condenser lens and for providing output electric signals by photoelectric converting means disposed along each axis of said pair of detecting means; and frame detecting means for detecting a position of a frame for supporting means for preventing adherence of foreign particles on said substrate.

16. A foreign particle detecting method comprising the steps of:

actuating one of a set of scanners to scan one half of a substrate to be inspected, the substrate having a frame with a pellicle mounted thereon, each scanner being positioned in a direction capable of scanning an opposite one half of the substrate to be inspected;

actuating the other of the set of scanners to scan the opposite one half of the substrate to be detected; and inspecting, during the actuation of each of the scanners, a respective one half of the substrate to be inspected using a respective one of a set of detectors positioned substantially at a right angle to the scanning direction, when viewed from above the substrate;

whereby the entirety of the substrate is enabled to be inspected for detection of foreign particles irrespective of the frame and pellicle mounted on the substrate.

17. A foreign particle detecting method according to claim 16, wherein each of the scanners has an optical axis arranged at an inclination angle of $22.5° \pm 15°$ with respect to the substrate.

18. A foreign particle detecting method according to claim 16, wherein each of the detectors has an optical axis arranged at an inclination angle of $22.5° \pm 5°$ with respect to the substrate.

19. A foreign particle detecting apparatus comprising:

a pair of light directing means disposed opposing to each other with respect to a substrate for directing a pair of light beams to the substrate in a direction inclined with respect to the substrate so as to enable light to be scattered from a particle on the substrate, the light directing means including;

a laser beam source, a rotating mirror for performing scanning of a laser beam produced from said laser beam source in a predetermined direction, a changeover mirror for changing over the direction of the laser beam reflected from the rotating mirror, table driving means for driving a table carrying the substrate so as to enable two-dimensional scanning of a part of the substrate with the scanning by the rotating mirror, and lens and mirrors set in a path of said laser beam from said laser beam source for polarizing and focusing the laser beam onto the substrate in the direction inclined with respect to the substrate, a pair of scattered light detecting means for detecting scattered light from the substrate and disposed opposing to each other and substantially at right angles with respect to said pair of light beams, each of said pair of light detecting means including;

a polarized light analyzer, a condenser lens, slit means for blocking light scattered from other than the surface of the substrate, and photoelectric converting means arranged along said scanning direction and inclined with respect to the substrate, set-up means for setting up at least four different foreign particle inspecting areas on the substrate including;

sensor means for detecting a metallic attachment for the substrate and for producing signals indicative of the detection result, and specifying means for specifying the presence or absence and the position of a foreign particle in the inspection area including determining means for determining position signals representing the position of the foreign particle when output signals of said sensor means are greater than a predetermined varying standard.

20. A foreign particle detecting apparatus according to claim 19, wherein the metallic attachment is a frame of a pellicle mounted on the substrate and which encloses the different inspection areas.

* * * * *